US00PP30696P2

(12) United States Plant Patent
Hartman

(10) Patent No.: US PP30,696 P2
(45) Date of Patent: Jul. 9, 2019

(54) ***CALADIUM* PLANT NAMED 'BOLD 'N BEAUTIFUL'**

(50) Latin Name: ***Caladium* X *hortulanum***
Varietal Denomination: Bold 'N Beautiful

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 15/732,916

(22) Filed: Jan. 13, 2018

(51) Int. Cl.
*A01H 6/10* (2018.01)

(52) U.S. Cl.
USPC ..... Plt./373

(58) Field of Classification Search
USPC ..... Plt./373
CPC ..... A01H 6/10; A01H 5/00; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Caladium* plant named 'Bold 'N Beautiful', characterized by its intermediate height and upright mounded plant habit; vigorous growth habit and very rapid growth rate; lance-type leaves that have dark green-colored margins, transitional areas that are white and dark green mosaic, pinkish red-colored venation and the areas adjacent to the veins and interveinal areas that are pinkish red in color; with high light conditions, interveinal areas can be mostly white and/or greenish white variably tinged with purplish or pinkish red; and petioles that are blackish green in color with tan orange-colored stripes, streaks and tessellations.

4 Drawing Sheets

Botanical designation: *Caladium* X *hortulanum*.
Cultivar denomination: 'BOLD 'N BEAUTIFUL'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'Bold 'N Beautiful'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium* X *hortulanum* 'White Star', disclosed in U.S. Plant Pat. No. 21,148, as the female, or seed, parent with *Caladium* X *hortulanum* 'Florida Red Ruffles', disclosed in U.S. Plant Pat. No. 13,136, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Bold 'N Beautiful'. These characteristics in combination distinguish 'Bold 'N Beautiful' as a new and distinct *Caladium* plant:

1. Intermediate in height and upright mounded plant habit.
2. Vigorous growth habit and very rapid growth rate.
3. Lance-type leaves that have dark green-colored margins, transitional areas that are white and dark green mosaic, pinkish red-colored venation and the areas adjacent to the veins and interveinal areas that are pinkish red in color; with high light conditions, interveinal areas can be mostly white and/or greenish white variably tinged with purplish or pinkish red.
4. Petioles that are blackish green in color with tan orange-colored stripes, streaks and tessellations.

Plants of the new *Caladium* differ primarily from plants of the female parent, 'White Star', in the following characteristics:

1. Plants of the new *Caladium* grow faster and finish about two weeks earlier than plants of 'White Star'.
2. Plants of the new *Caladium* and 'White Star' differ in leaf color as leaves of 'White Star' are white to grey-green in color with pink to light pink-colored veins and dark green-colored borders.

Plants of the new *Caladium* differ primarily from plants of the male parent, 'Florida Red Ruffles', in the following characteristics:

1. Plants of the new *Caladium* are taller than plants of 'Florida Red Ruffles'.
2. Plants of the new *Caladium* grow faster and finish about two weeks earlier than plants of 'Florida Red Ruffles'.

3. Plants of the new *Caladium* and 'Florida Red Ruffles' differ in leaf color as leaves of 'Florida Red Ruffles' have dark red-colored venation and interveinal areas and green-colored borders.

Plants of the new *Caladium* can be compared to plants of *Caladium* X *hortulanum* 'White Delight', disclosed in U.S. Plant Pat. No. 21,216. In side-by-side comparisons, plants of the new *Caladium* differ primarily from plants of 'White Delight' in the following characteristics:

1. Plants of the new *Caladium* are more mounding than and not as upright as plants of 'White Delight'.
2. Plants of the new *Caladium* grow faster and finish about two weeks earlier than plants of 'White Delight'.
3. Plants of the new *Caladium* and 'White Delight' differ in leaf color as leaves of 'White Delight' are white to grey-green in color with white-colored main veins and dark green-colored borders.
4. Plants of the new *Caladium* and 'White Delight' differ in leaf petiole color as leaf petioles of 'White Delight' are olive green in color with darker green-colored tessellations.

Plants of the new *Caladium* can be compared to plants of *Caladium* X *hortulanum* 'White Wonder', disclosed in U.S. Plant Pat. No. 21,044. In side-by-side comparisons, plants of the new *Caladium* differ primarily from plants of 'White Wonder' in the following characteristics:

1. Plants of the new *Caladium* are taller than plants of 'White Wonder'.
2. Plants of the new *Caladium* and 'White Wonder' differ in leaf color as leaves of 'White Wonder' are white to grey-green in color with light pink to white-colored venation and dark green-colored borders.
3. Plants of the new *Caladium* and 'White Wonder' differ in leaf petiole color as leaf petioles of 'White Wonder' are tan green in color with darker green-colored stripes.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Bold 'N Beautiful' in a container and grown in a shadehouse (tuber de-eyed).

The photograph at the top of the second sheet is a comparison view of typical potted plants of the female parent, 'White Star' (left), 'Bold 'N Beautiful' (center) and the male parent, 'Florida Red Ruffles' (right).

The photograph at the bottom of the second sheet is a comparison view of typical potted plants of 'White Wonder' (left), 'Bold 'N Beautiful' (center) and 'White Delight' (right).

The photograph at the top of the third sheet is a comparison view of typical plants of 'Bold 'N Beautiful' grown in containers; the plant on the left has not had its tuber de-eyed and the plant on the right has had its tuber de-eyed prior to planting.

The photograph at the bottom of the third sheet is a close-up view of typical freshly-harvested tubers with roots and leaf petioles of 'Bold 'N Beautiful'.

The photograph on the fourth sheet is a side perspective view of typical plants of 'Bold 'N Beautiful' grown in an open field.

DETAILED BOTANICAL DESCRIPTION

The aforementioned photographs and following observations and measurements describe plants grown in 15-cm containers in a polypropylene-covered shadehouse (50% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels were about 10,000 to 12,000 foot-candles. Plants grown in the shadehouse were five weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Bold 'N Beautiful'.

Parentage:

*Female, or seed, parent.*—*Caladium* X *hortulanum* 'White Star', disclosed in U.S. Plant Pat. No. 21,148.

*Male, or pollen, parent.*—*Caladium* X *hortulanum* 'Florida Red Ruffles', disclosed in U.S. Plant Pat. No. 13,136.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments ovate to elliptic in shape. Height: About 3.2 cm. Diameter: About 4 cm to 5.5 cm. Segment height: About 2.3 cm. Segment diameter: About 3 cm. Axillary buds size: About 4 mm by 5 mm. Texture: Thick, starchy; somewhat brittle. Color: Epidermis, freshly-harvested: Close to 199A, 199B and 158D. Epidermis, dried: Close to 200A and 200B. Cortical tissue: Close to 2D. Axillary buds: Close to N155C. Root description: Thick, fleshy contractile roots with few lateral branches; close to N155D in color. Rooting habit: Sparse to medium density.

Plant description:

*Plant type.*—Herbaceous perennial; suitable as a potted plant in containers 15-cm to 25-cm and suitable as a landscape plant in shaded areas.

*Plant and growth habit.*—Intermediate in height and upright mounded plant habit; vigorous growth habit and very rapid growth rate; potted plants in finished or saleable form in about five to six weeks after planting tubers; leaf petioles and leaves arise from one or more growing points on tubers; leaf petioles initially upright and outwardly leaning and arching with development.

*Plant height, from soil level to top of foliar plane, shadehouse-grown potted plants.*—About 24 cm to 28 cm.

*Plant diameter or spread, shadehouse-grown potted plants.*—About 32 cm to 38 cm.

*Number of shoots per plant, shadehouse-grown potted plants, tubers not de-eyed.*—About three develop per #1 tuber.

*Number of shoots per plant, shadehouse-grown potted plants, tubers de-eyed.*—About three to four develop per #1 tuber.

*Cataphylls, shadehouse-grown potted plants.*—Length: About 5.5 cm to 9.7 cm. Width: About 1 cm to 1.4 cm. Shape: Wedge or strap-shaped. Apex: Acuminate to acute. Base: Sheathing the stem. Color, inner surface: Close to N155C; colors and patterns on the outer surface are visible on the inner surface. Color, outer surface: Close to 200A and 202A streaked and stippled with close to 159D tinged with close to 147C; with development, color becoming closer to 199A stained with close to 187A.

Leaf description:

*Arrangement and type.*—Alternate; simple; lance-type.

*Length, shadehouse-grown potted plants.*—About 18 cm to 24.5 cm.

*Width, shadehouse-grown potted plants.*—About 12.5 cm to 17.5 cm; when flattened, about 13 cm to 19 cm.

*Shape.*—Ovate to cordate.

*Apex.*—Acuminate to acute.

*Base.*—Sagittate to peltate.

*Margin.*—Entire; wavy with broad undulations.

*Texture and luster, upper and lower surfaces.*—Smooth, glabrous; dull sheen.

*Texture and luster, lower surface.*—Smooth, glabrous; dull sheen and venation, glaucous.

*Venation pattern.*—Pinnate.

*Color, field-grown plants.*—Developing and fully developed leaves, upper surface: Background color: Close to 147A and 147B. Margins: Close to 147A and 147B; thin leaf edge, close to 187A. Basal notch: Close to 183A to 183B and 187B. Midvein and primary venation: Close to 185D, 184A, N155D or N155B. Interveinal areas: Close to 155C or 155C tinged with close to 147D. Random spots and splotches along venation: Close to 185B. Developing and fully developed leaves, lower surface: Background color: Close to 191A. Margins: Close to 191A; thin leaf edge, close to 187A. Basal notch: Close to 183A to 183B and 187B. Midvein and primary venation: Close to 155A to 155C variably tinged with close to 49D or 50D. Interveinal areas: Close to 155A to 155C variably tinged with close to 49D or 50D. Transitional areas: Close to 147B to 147C and 146B.

*Color, shadehouse-grown potted plants.*—Developing and fully developed leaves, upper surface: Background color: Close to 147A. Margins: Close to 147A; thin leaf edge, close to 187A. Basal notch: Close to 187B and 185A. Midvein and primary venation: Close to 53A tinged with close to 183A. Secondary venation: Close to 155C with streaks and flecks of close to 48A to 48B; or close to 48B to 48C with flecks of close to 155C. Center and areas surrounding main veins: Close to 47A to 47B. Interveinal areas: Close to 155C, 155D, 147A and 147B mosaic. Transitional areas: Close to 155C, 147A, 147B and 139A mosaic. Developing and fully developed leaves, lower surface: Background color: Close to 147A. Margins: Close to 147A; thin leaf edge, close to 187B. Basal notch: Close to 187B. Midvein and primary venation: Close to 194C to 194D tinged with close to 160D with variable flecks and streaks, close to 200D or close to 200D tinged with close to 147B to 147C. Center and areas surrounding main veins: Close to 53A. Interveinal areas: Close to 56D, 56B to 56C or lighter than 49D. Transitional areas: Close to 191A or 194B.

*Petioles.*—Aspect: Initially upright and straight and outwardly leaning and arching with development; flexible. Length, shadehouse-grown potted plants: About 18 cm to 24 cm. Diameter, distally, shadehouse-grown potted plants: About 4.5 mm. Diameter, proximally, shadehouse-grown potted plants: About 7 mm to 9 mm. Texture: Smooth, glabrous. Color, shadehouse-grown potted plants: When developing: Close to N170D tinged with close to 36D and streaked, striped, stippled and tessellated with close to 200B to 200C tinged with close to 147A. Fully developed: Close to 200A and 202A tinged with close to 147A and stippled, striped and streaked with close to N170D and 27D; below the leaf and petiole junction, close to N170D tinged with close to 36D and streaked and stippled with close to 200B to 200C. Wing length, shadehouse-grown potted plants: About 5.7 cm to 8 cm. Wing diameter, shadehouse-grown potted plants: About 7 mm. Texture and luster, inner and outer surfaces: Smooth, glabrous; dull to somewhat glossy. Wing color, shadehouse-grown potted plants: Inner surface: Close to N155C; colors and patterns on the outer surface are visible on the inner surface. Outer surface: Close to 200A tinged with close to 147A, marbled with close to 159D tinged with close to 27D, and streaked and stippled with close to 200A and tinged with close to 147A.

Inflorescence description: Inflorescence initiation and development have not been observed on plants of the new *Caladium* to date.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'Bold 'N Beautiful' as illustrated and described.

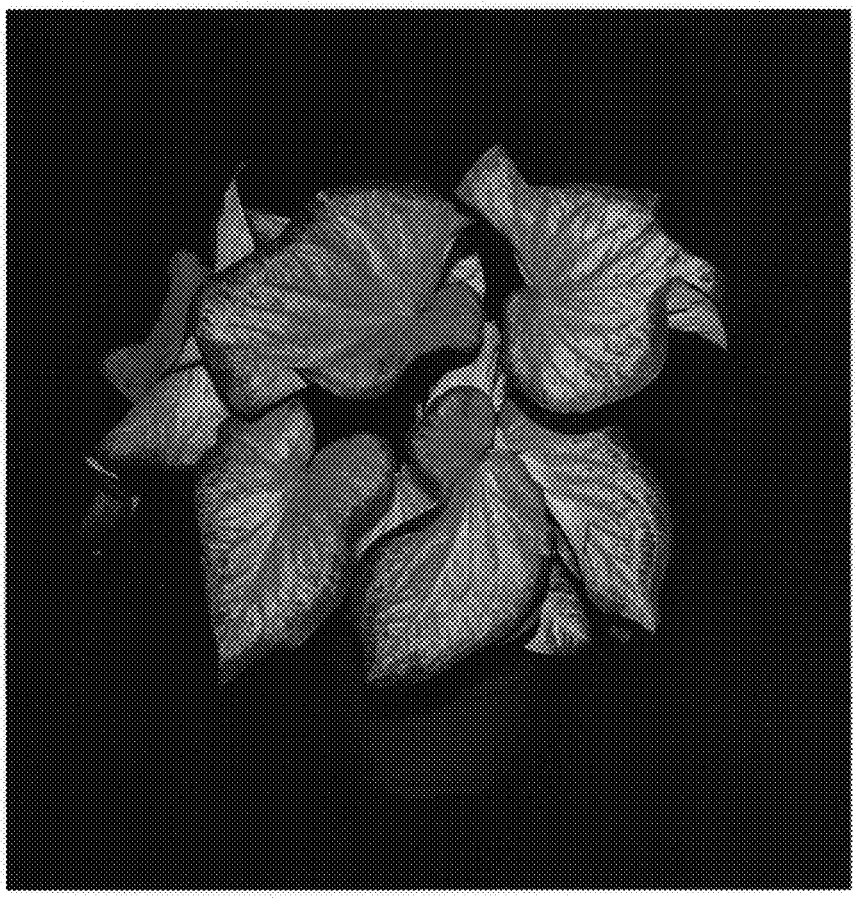

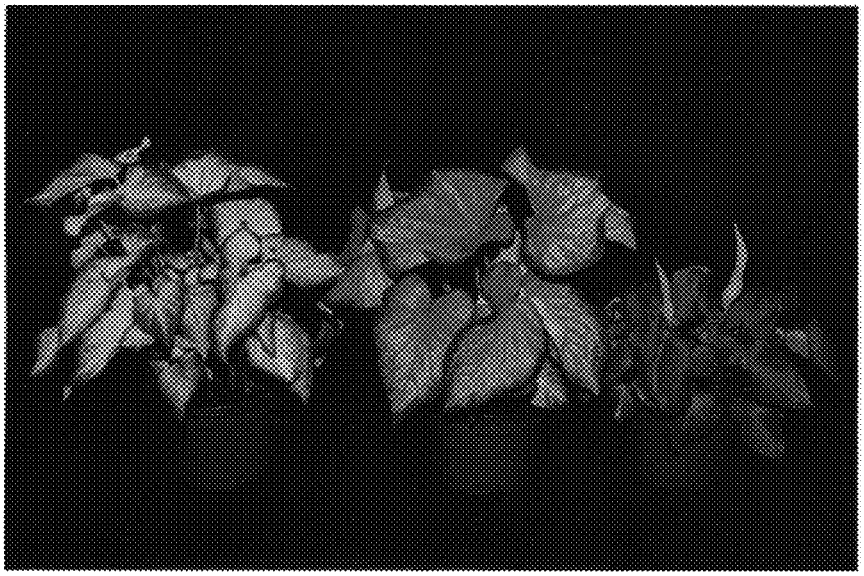
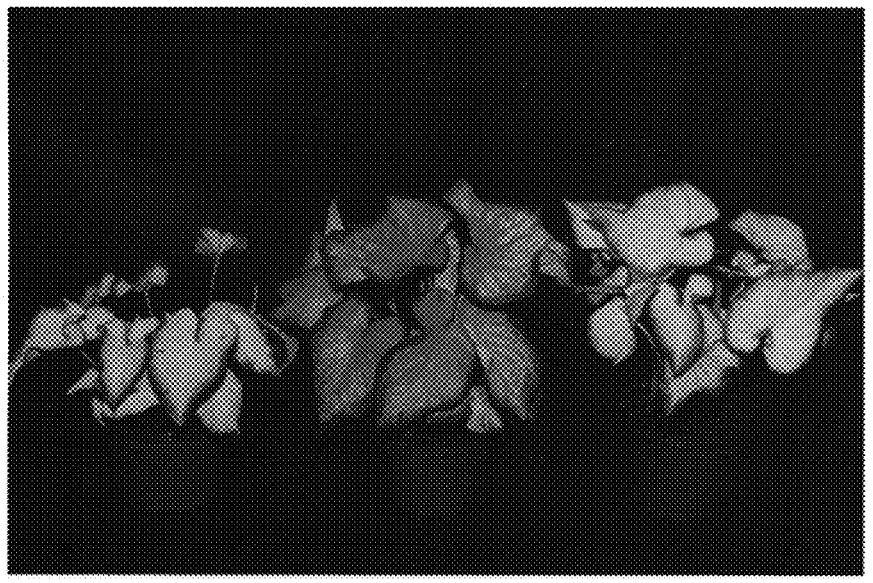

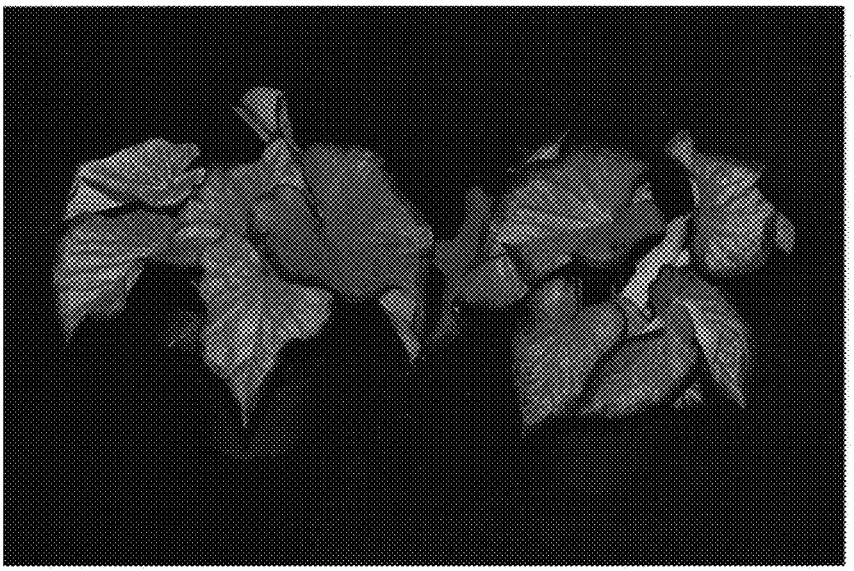
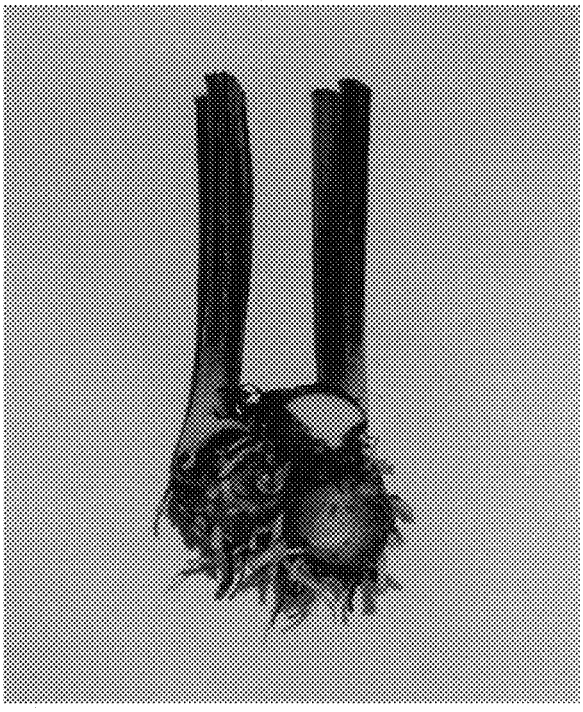

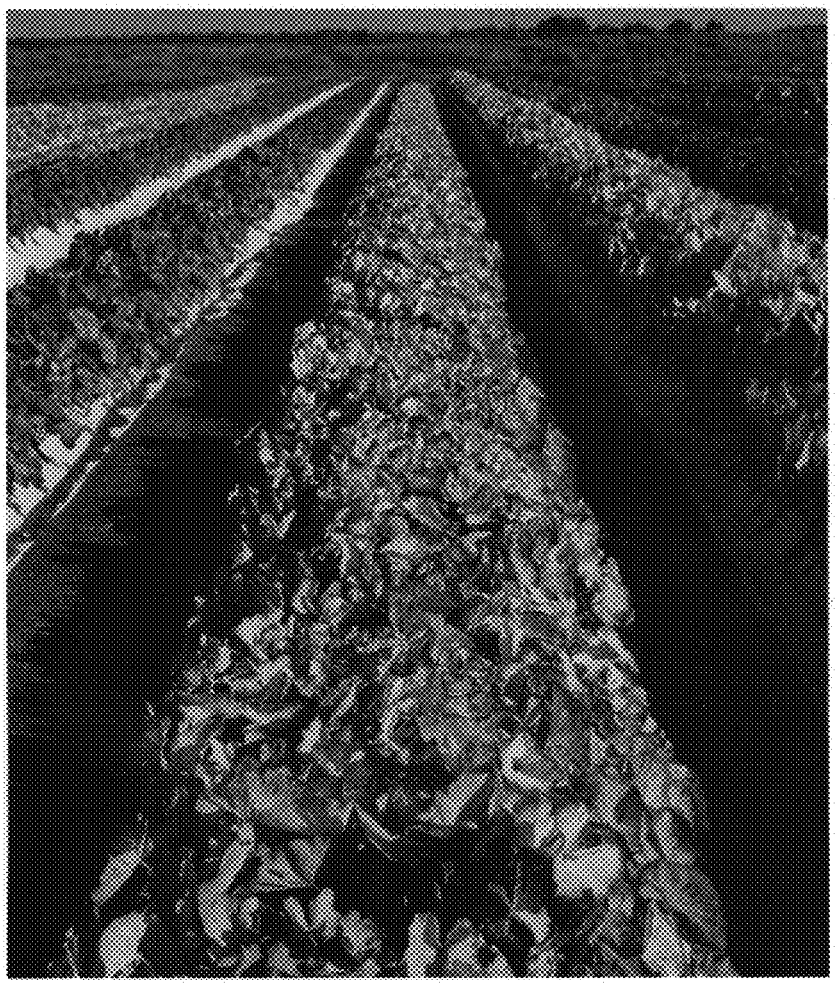

* * * * *